United States Patent [19]
Raulerson et al.

[11] Patent Number: 6,040,695
[45] Date of Patent: Mar. 21, 2000

[54] METHOD AND APPARATUS FOR INSPECTION OF COMPONENTS

[75] Inventors: David A. Raulerson, Palm Beach Gardens; Jay Amos, Hobe Sound; Kevin D. Smith, Jupiter, all of Fla.

[73] Assignee: United Technologies Corporation, Hartford, Conn.

[21] Appl. No.: 08/996,127

[22] Filed: Dec. 22, 1997

[51] Int. Cl.[7] ........................... G01R 33/12; G01N 27/72
[52] U.S. Cl. ............................ 324/240; 324/262
[58] Field of Search ..................... 324/239, 240, 324/241, 242, 243, 262; 336/232

[56] References Cited

U.S. PATENT DOCUMENTS

| | | | |
|---|---|---|---|
| 3,061,775 | 10/1962 | Reznowski | 324/239 |
| 3,242,426 | 3/1966 | Burbank | 324/240 |
| 5,047,719 | 9/1991 | Johnson et al. | 324/242 |

*Primary Examiner*—Walter E. Snow

[57] ABSTRACT

An eddy current probe for use in inspecting an object, includes a driver having a coil with an effective coil axis, and further includes a receiver having a coil with a coil axis oriented substantially perpendicular to the driver coil effective coil axis, the receiver having a length, and a width, the length being the dimension in the direction parallel to the scanning path, and the width having a dimension magnitude substantially greater than that of the length. A method for inspecting an object uses such an eddy current probe. An eddy current probe for use in inspecting an object, includes a driver having a coil with an effective coil axis, the driver having a length and a width, the length being the dimension in a direction substantially parallel to a scanning path, and further includes a receiver having a coil with a coil axis oriented substantially perpendicular to the driver coil effective coil axis, where the magnitude of a distance between the receiver and at least one of the edges is less than 0.125 times the width of the driver. A method for inspecting an object uses such an eddy current probe.

29 Claims, 12 Drawing Sheets

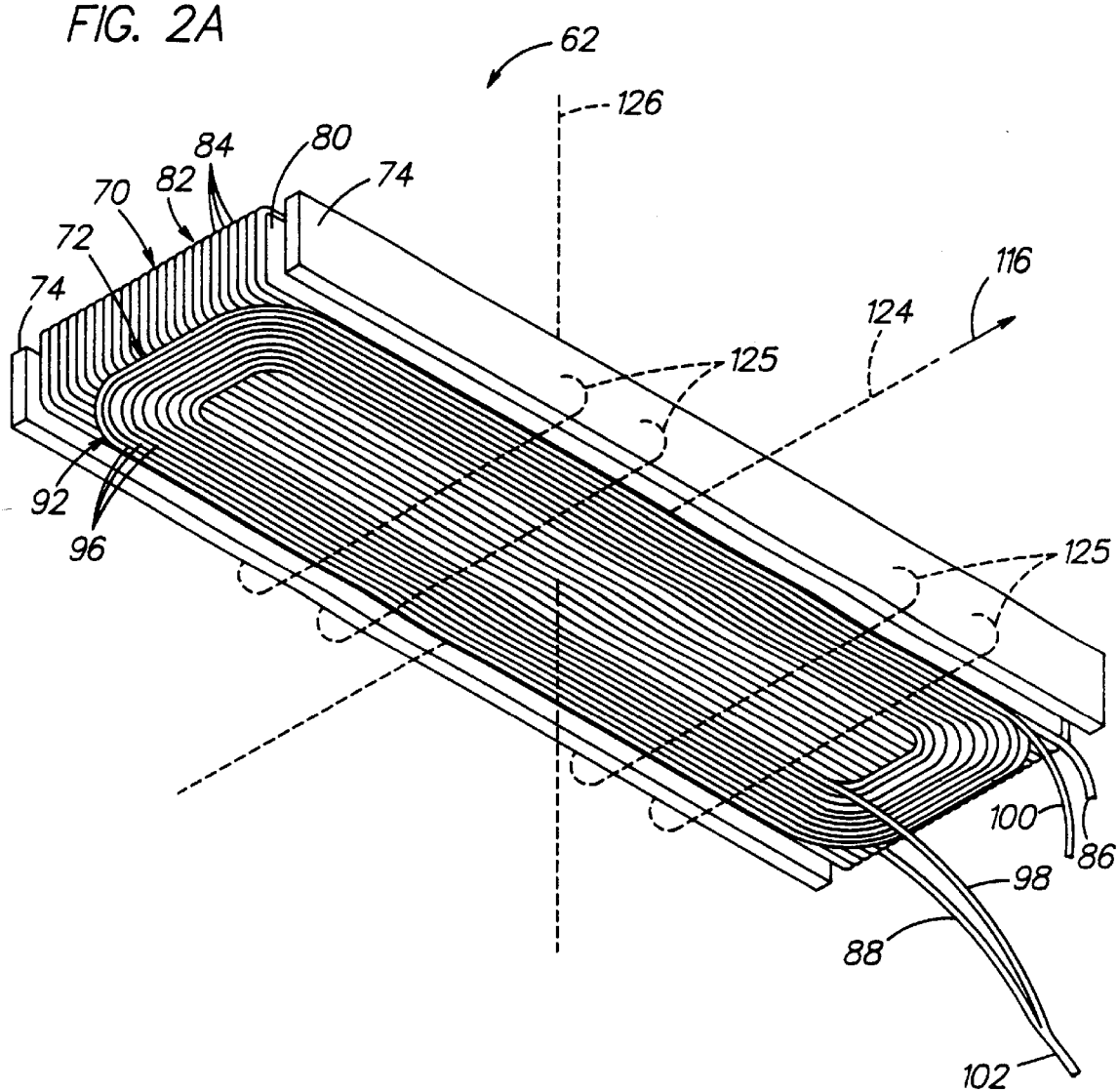

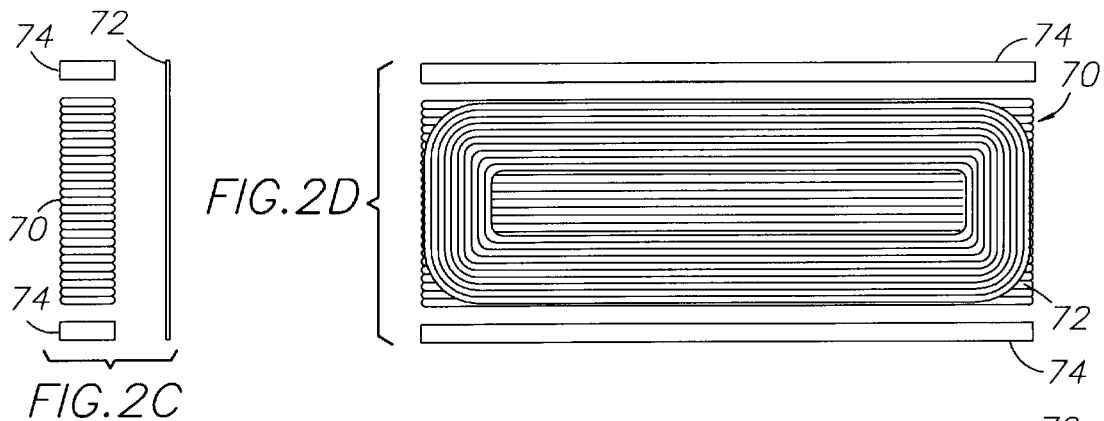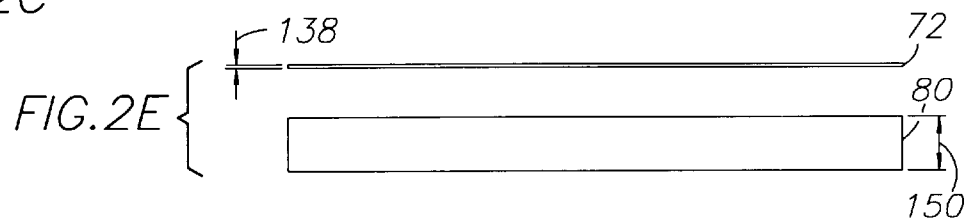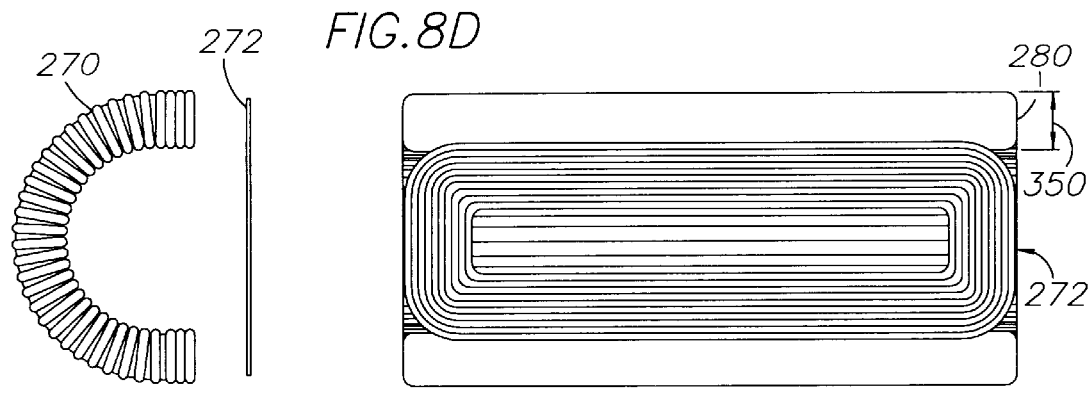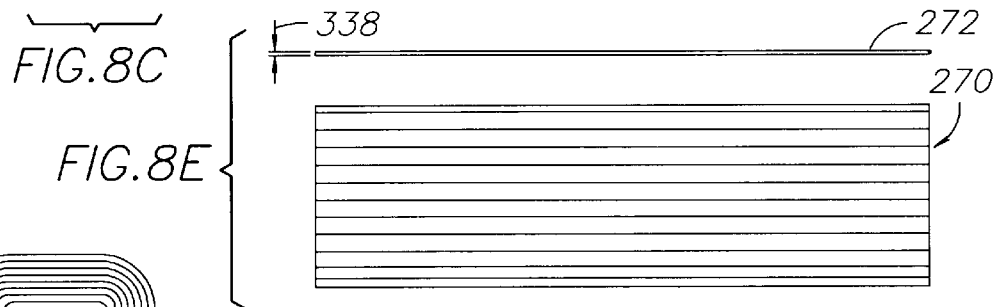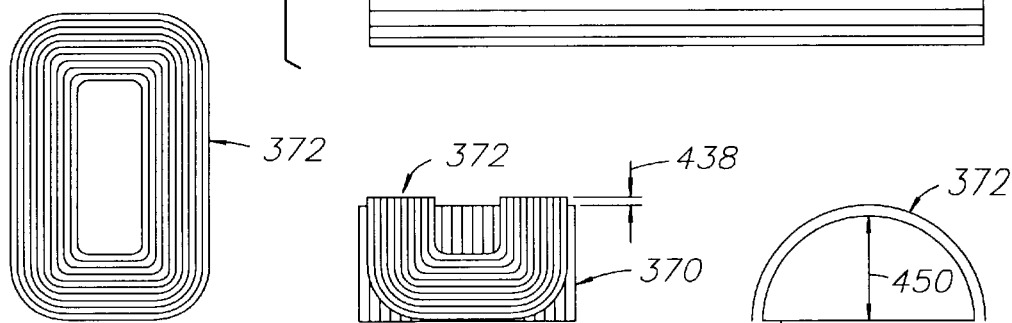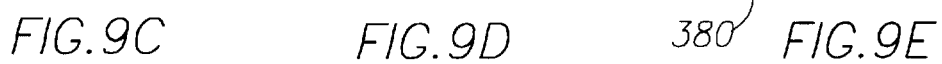

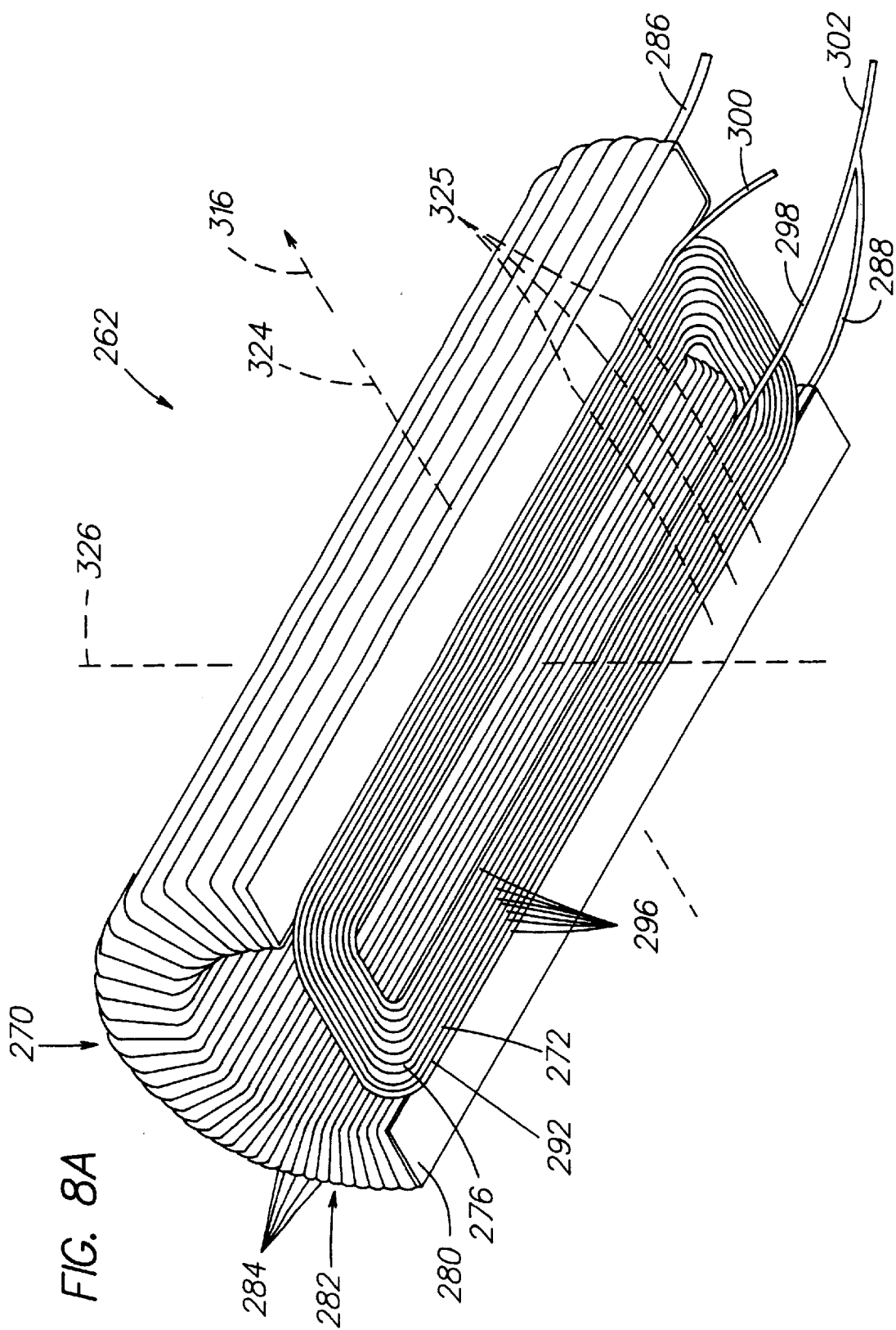

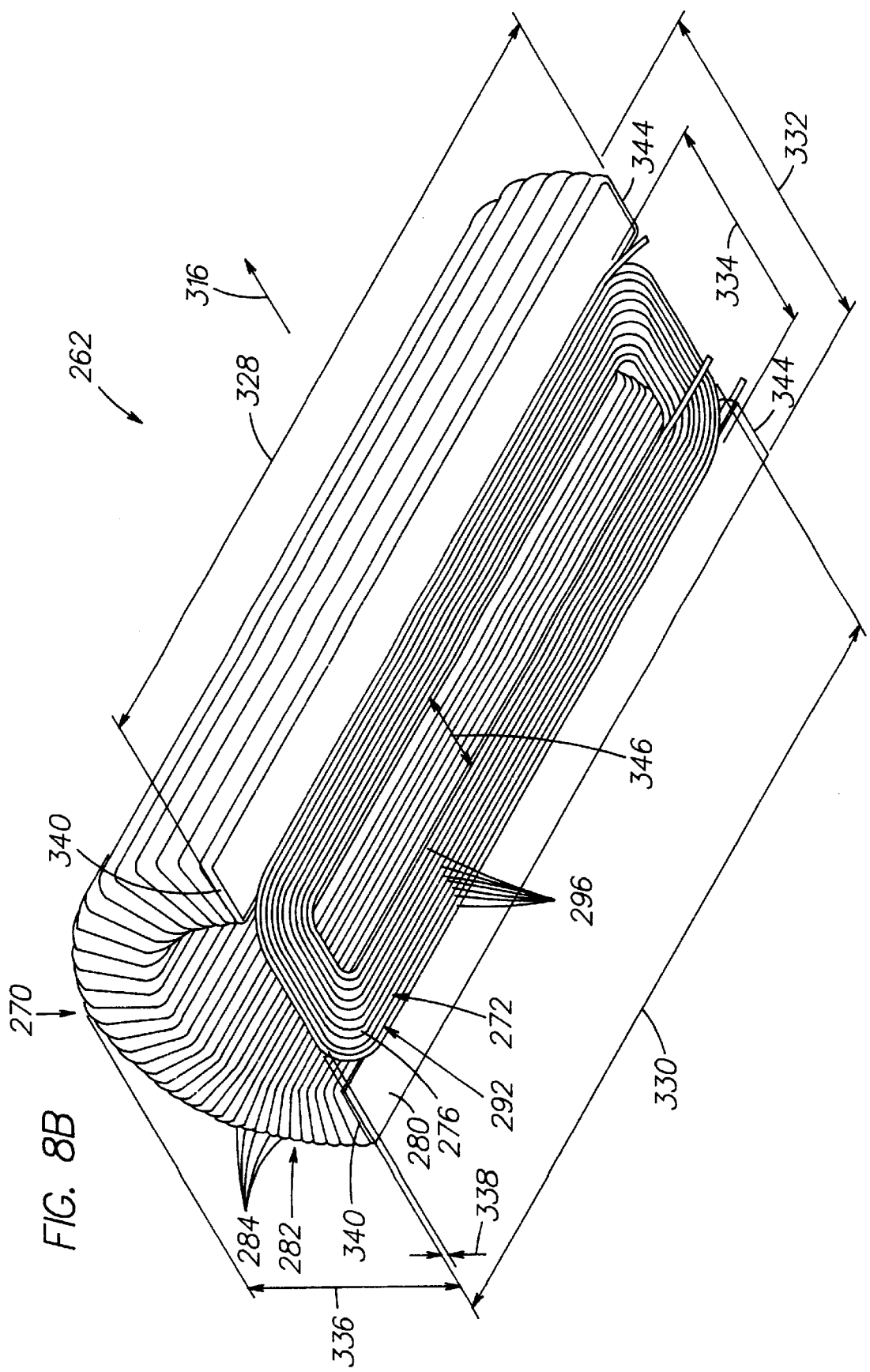

6,040,695

METHOD AND APPARATUS FOR INSPECTION OF COMPONENTS

TECHNICAL FIELD

This invention relates to methods and apparatus for inspection of components, more particularly, to methods and apparatus that employ eddy current technology.

BACKGROUND

Eddy current probes are often used for non-destructive evaluation of critical components in the aerospace and power generation industries. Many of these critical components must endure extremely high stresses in the course operation. In the gas turbine engine industry, increases in thrust to weight ratios and increases in duration between inspections require even greater durability to assure reliable engine operation. It is necessary to detect even small flaws in order to ensure the durability of the component. For example, a rotor disk for a gas turbine engine must have its entire surface inspected in order to detect the presence of defects. An inability to detect flaws of a certain size can prevent production of higher performance and more competitive products. Moreover, the surfaces on these critical components often have curves, corners, and/or irregular shapes, i.e. complex geometry, maling them even more difficult to inspect.

An eddy current probe typically includes a driver coil and a receiver coil. When provided with an electrical excitation current, the driver coil generates an alternating electromagnetic magnetic field that results in a magnetic field in a component under inspection, which in turn results in an eddy current within the component. The eddy current in the component results in a electromagnetic signal or response, within the receiver coil, detected by commercial instrumentation. As the probe passes over an anomaly, e.g., a flaw or a different morphology, in the component, the anomaly disrupts the eddy current, thereby resulting in a different signal within the receiver coil. The change is detected by the instrumentation.

Two criteria commonly used for appraising an eddy current probe include the sensitivity of its response, and the uniformity of its response as measured at different points along the width of the probe, referred to herein as uniformity. Sensitivity is a qualitative measure that indicates the capability of the probe to detect flaws of a particular size. For a probe to be useful for an application, it must have sufficient sensitivity to detect flaw sizes of interest. Uniformity is an indication of the useful width of the probe. Probes do not have the same sensitivity at all points across the width of the probe. The sensitivity at the edge is typically lower than at the center and may not be suitable for the application. A greater useful width, in effect means that the probe inspects a wider area at one time, referred to as wider field coverage, enabling a more rapid overall inspection. Uniformity is also an indication of the usefulness of the probe for inspecting components having complex geometries, for example those having corners. Typically, the edge is the only part of the probe that can be positioned near a corner. If the probe has low sensitivity at its edges, the probe will not be able to detect a flaw near the corner.

Traditionally, the only eddy current probes having suitable sensitivity for use in inspecting a rotor disk have had very small probe elements, e.g., 0.030 to 0.060 inches wide. The use of probes with such small elements greatly increases the time and cost required for inspection. Even with fully automated scanning systems, the inspection of a single rotor disk currently takes over 80 hours due to the narrow useful width, i.e., narrow field coverage, of these small probes.

Eddy current probes capable of inspecting a wide area on a component, i.e., wide field coverage, are known. Such probes, commonly referred to as wide field eddy current probes, are wider than an ordinary eddy current probe. Greater width provides the probe with greater surface area to thereby inspect a wider surface area on the component. However, as a result of the greater width and surface area, present day wide field eddy current probes have insufficient sensitivity for inspection of many critical components in aerospace and power generation industries. Furthermore most wide field eddy current probes do not provide a sufficiently uniform response, the sensitivity of the probe decreases excessively near the edges. As such, they are not well adapted to inspecting surfaces with complex geometries, e.g., those having corners.

U.S. Pat. Nos. 5,442,286 to Sutton, Jr. et al., and U.S. Pat. No. 5,262,722 to Hedengren et al. disclose eddy current probes having eddy current probe elements disposed within thin multi-layer structures. The driver and the receiver are disposed on adjacent layers in the structure. Such probes are well adapted to inspecting complex geometries, but they often have less than desired sensitivity, e.g., low signal to noise ratio.

Another type of eddy current probe is referred to as an electric current perturbation probe. In a perturbation probe, the driver core axis is perpendicular to the receiver core axis. This feature decouples the receiver magnetic field from the driver magnetic field, thereby reducing the sensitivity of the receiver to surface noise that does not represent a defect. Some materials, for example titanium, present more surface noise than others. Perturbation probes typically provide high sensitivity but do not provide wide field coverage and are not adapted to inspecting complex geometries.

Hoshikaw et al. ("A NEW ECT PROBE WITH ROTATING DIRECTION EDDY CURRENT", Koyama et al,. Review of Progress in Quantitative Nondestructive Evaluation, Vol. 15; "BASIC STUDY OF A NEW ECT PROBE USING UNIFORM ROTATING DIRECTION EDDY CURRENT", Koyama et al., Vol. 16) disclose one type of perturbation probe referred to as an eddy current tester and probe employing a rotating direction eddy current. The probe employs a driver having a cube shape, 30 mm on a side, with two orthogonal windings, and a pancake receiver. Hoshikaw et al. discloses that the probe generates a large amount of data on a flaw with minimal noise. However, this probe does not provide a wide inspection field, nor is it adapted to inspecting complex geometries.

U.S. Pat. No. 5,483,160 to Gulliver et al. disclose a multi-sensor probe having a driver coil and one or more, e.g. four, perturbation coils, i.e. receiver coils with axes perpendicular to that of the driver coil. The perturbation coils each have a flat shape and are mounted on adjacent facets of a probe head. The perturbation coils are longer (dimension parallel to direction of movement of probe relative to component) than they are wide (dimension perpendicular to direction of movement of probe relative to component). However, this probe is not a wide field probe nor is it likely to have suitable sensitivity for use in inspecting critical components.

SUMMARY OF THE INVENTION

An object of the present invention is to provide an eddy current probe that has good sensitivity yet provides a wide inspection field.

Another object of the present invention is to provide an eddy current probe for use in inspecting components having a complex geometry.

According to a first aspect of the present invention, an eddy current probe for use in inspecting an object, where the probe is moved along a scan path relative to the object, includes a driver having a coil with an effective coil axis, the driver having a length and a width, the length being the dimension in a direction substantially parallel to the scanning path, and further includes a receiver having a coil with a coil axis oriented substantially perpendicular to the driver coil effective coil axis, the receiver having a length, a width, and a thickness, the length being the dimension in the direction parallel to the scanning path, the width having a dimension magnitude substantially greater that of the length.

According to a second aspect of the present invention, an eddy current probe for use in inspecting an object, where the probe is moved along a scan path relative to the object, includes a driver having a coil with an effective coil axis, the driver having a length and a width, the length being the dimension in a direction substantially parallel to the scanning path, the coil having widthwise opposite edges, and further includes a receiver having a coil with a coil axis oriented substantially perpendicular to the driver coil effective coil axs, the receiver having a length, a width, and a thickness, the length being the dimension in the direction parallel to the scanning path, where the magnitude of a distance between said receiver and at least one of said edges is less than 0.125 times the width of said driver.

According to a third aspect of the present invention, a method for inspecting an object along a scan path relative to the object, includes providing an eddy current probe having a driver having a coil with an effective coil axis, the driver having a length and a width, the length being the dimension in a direction substantially parallel to the scanning path, and further having a receiver having a coil with a coil axis oriented substantially perpendicular to the driver coil effective coil axis, the receiver having a length, a width, and a thickness, the length being the dimension in the direction parallel to the scanning path, the width having a dimension magnitude substantially greater than that of the length, and further includes moving the eddy current probe substantially along the scan path, wherein the eddy current probe produces an electrical signal indicative of the presence of flaws in the object; and further includes presenting said eddy current signal.

According to a fourth aspect of the present invention, a method for inspecting an object along a scan path relative to the object, includes providing an eddy current probe having a driver having a coil with an effective coil axis, the driver having a length and a width, the length being the dimension in a direction substantially parallel to the scanning path, the coil of the driver having widthwise opposite edges, and further having a receiver having a coil with a coil axis oriented substantially perpendicular to the driver coil effective coil axis, the receiver having a length, a width, and a thickness, the length being the dimension in the direction parallel to the scanning path, where the magnitude of a distance between said receiver and at least one of said edges is less than 0.125 times the width of said driver, and further includes moving the eddy current probe substantially along the scan path, wherein the eddy current probe produces an electrical signal indicative of the presence of flaws in the object; and further includes presenting said electrical signal from said eddy current probe.

Although eddy current probes having perpendicularly oriented driver and receiver coil axes, i.e., electric current perturbation probes, are known, until now, it was not recognized that a perturbation probe could provide a wide inspection field with suitable sensitivity, e.g., for use in aerospace and or power generation industries. Increasing the width relative to the length, of an eddy current probe, to provide a wide field of coverage typically results in a significant and/or excessive degradation in sensitivity and uniformity of response across the width of the probe. However, it has been determined that for an electric current perturbation type, it is possible to increase the width of an relative to its length, to provide a wider field of coverage, without resulting in an excessive degradation in sensitivity or uniformity. Such a probe is useful for example in inspecting critical components in aerospace and power generation industries.

Furthermore, the conventional wisdom regarding perturbation probes has been that the width of the driver must be significantly greater than the width of the receiver in order to generate a sufficiently uniform magnetic field under the receiver. Traditionally, the width of the receiver is no more than ⅔ times that of the driver. As a result traditional perturbation probes have poor sensitivity near their widthwise edges, thereby limiting their useful width and their ability to inspect objects having complex geometries. However, it has been determined that the receiver can extend near a widthwise edge of the driver without excessively decreasing the uniformity of the magnetic field under the receiver. With a receiver near the widthwise edge of the driver and a suitable magnetic field under the receiver, there is greater sensitivity near the widthwise edges of the probe. Such a probe is useful for example for inspecting components having complex geometries.

BRIEF DESCRIPTION OF THE DRAWINGS

FIG. 2A is a perspective view of the eddy current probe element of FIG. 1A;

FIG. 2C is an exploded end view of the eddy current probe element of FIG. 1A;

FIG. 2D is an exploded plan view of the eddy current probe element of FIG. 1A;

FIG. 2E is an exploded side view of the driver core and the receiver of the eddy current probe element of FIG. 1A;

Figure 1A:
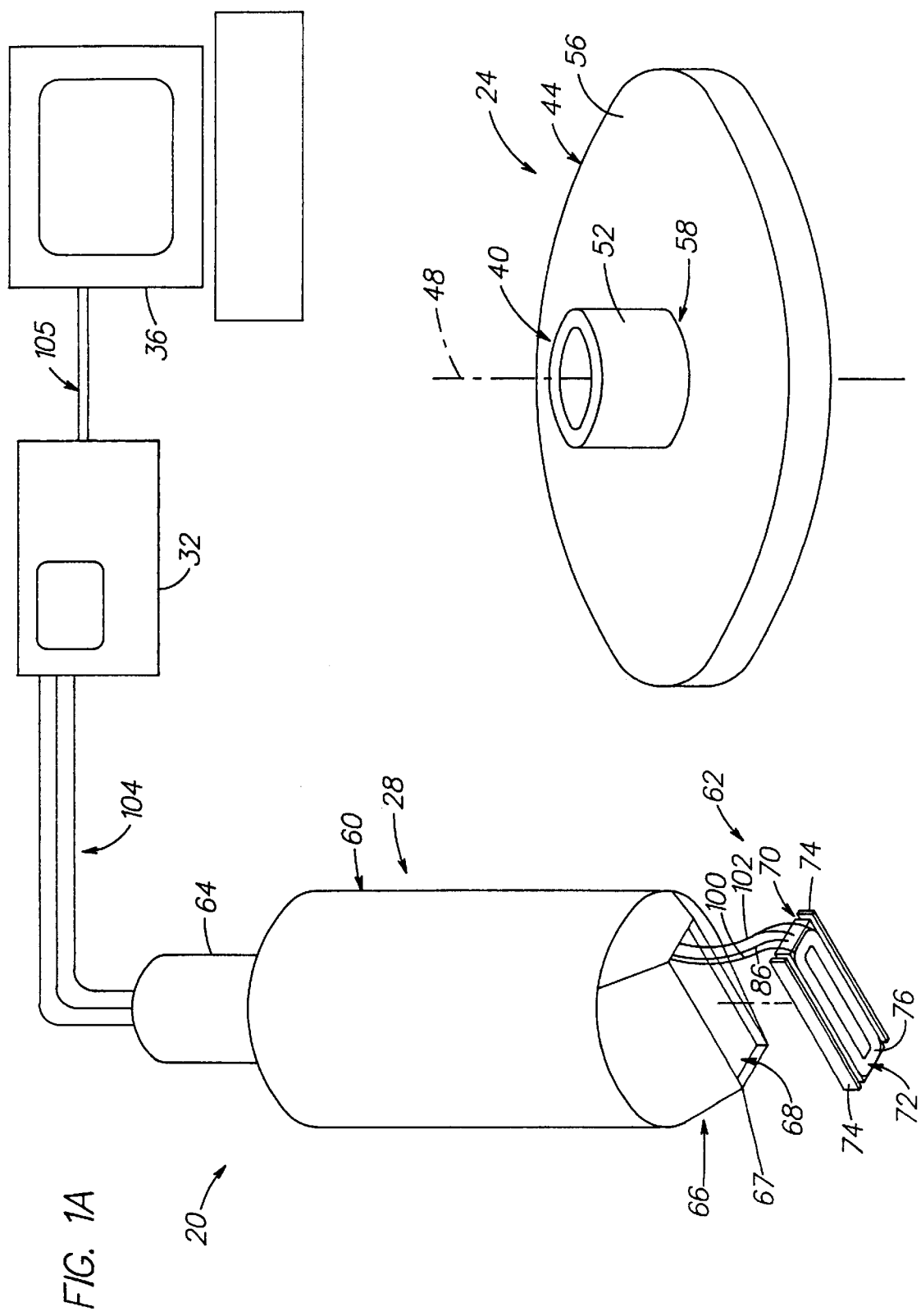
FIG. 1A is a combination of a perspective view of a rotor disk for a gas turbine engine and an eddy current probe according to a first embodiment of the present invention, in combination with a simplified schematic representation of an interface instrument and a processor for receiving and evaluating signals received from the eddy current probe.
Figure 4:
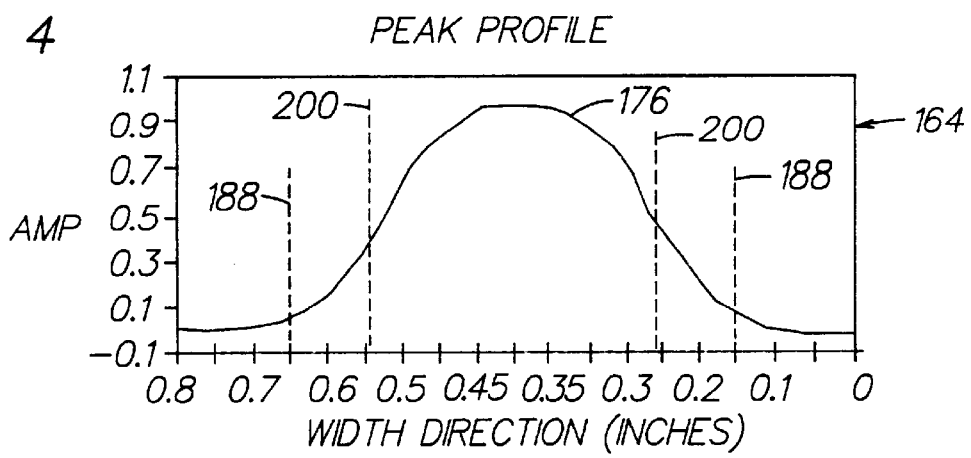
Figure 5:
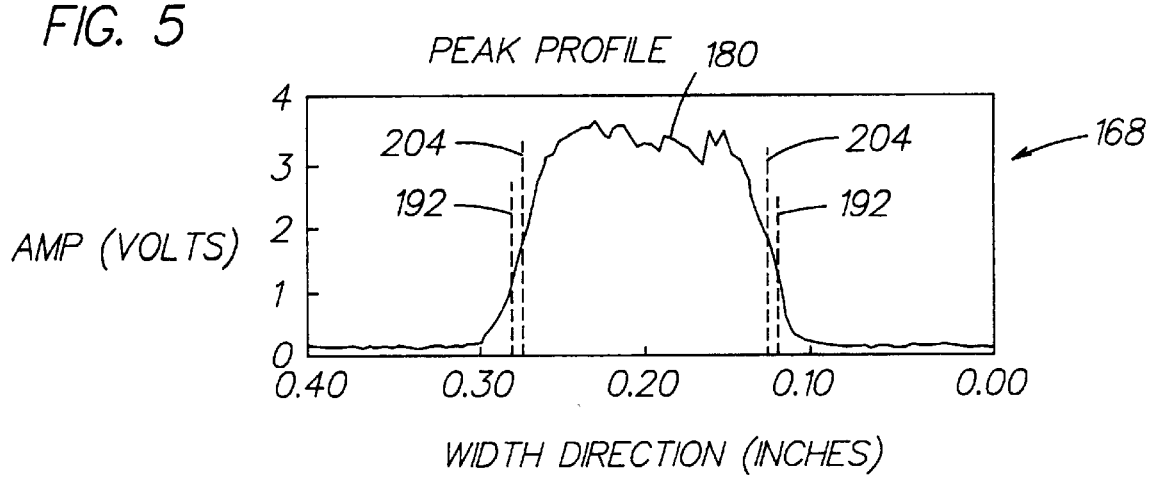
Figure 6:
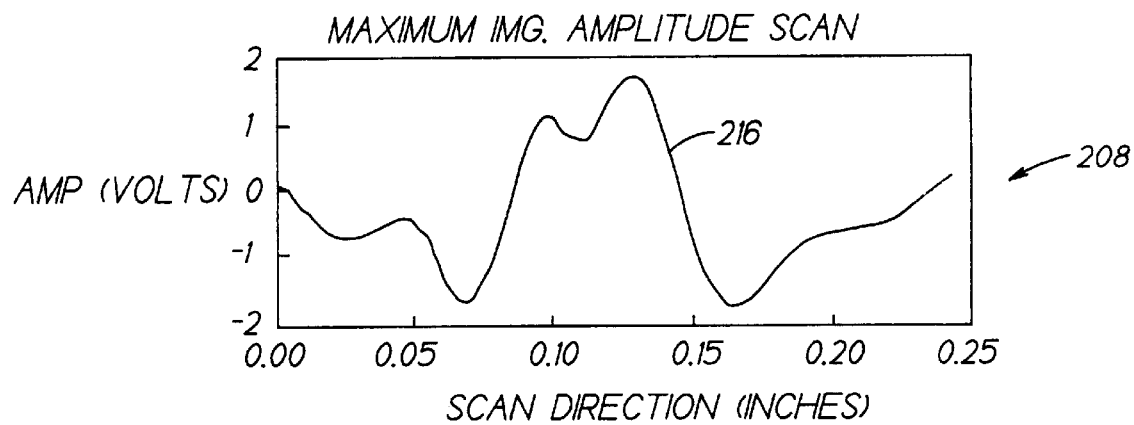
Figure 7:
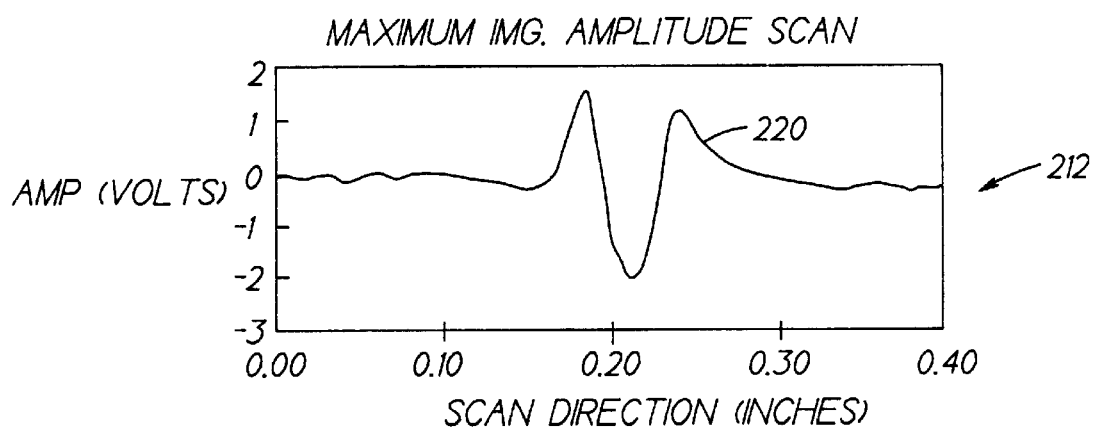
Figure 9A:
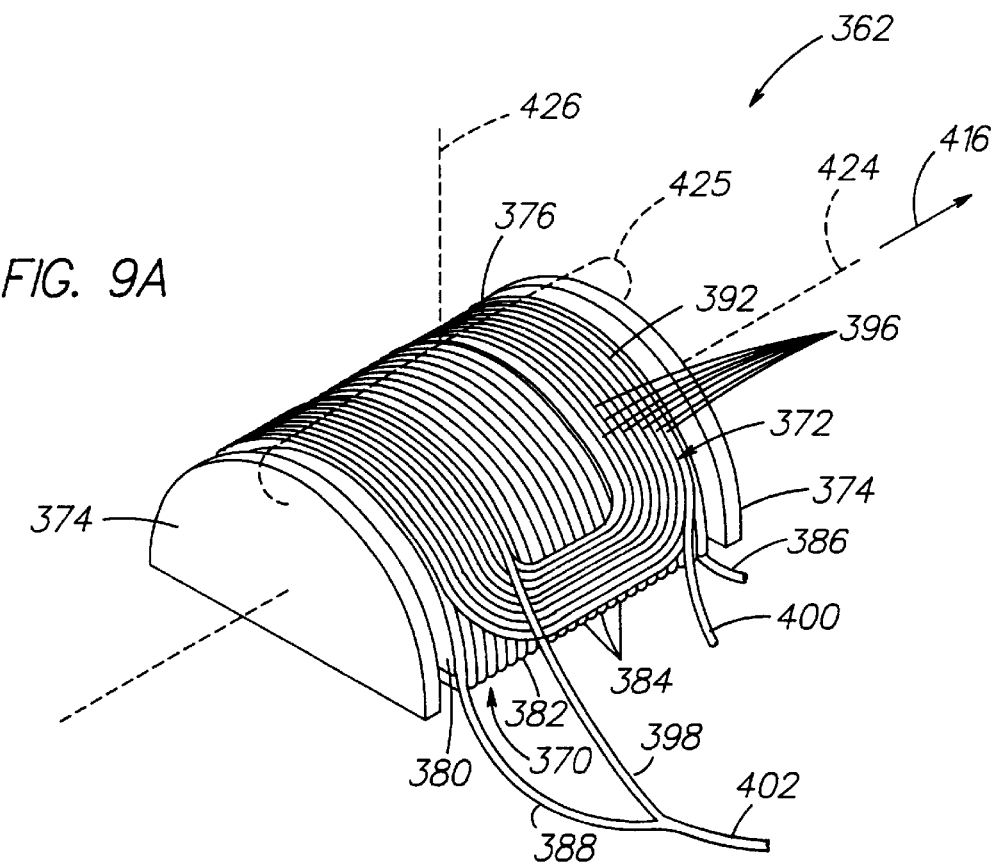
Figure 9B:
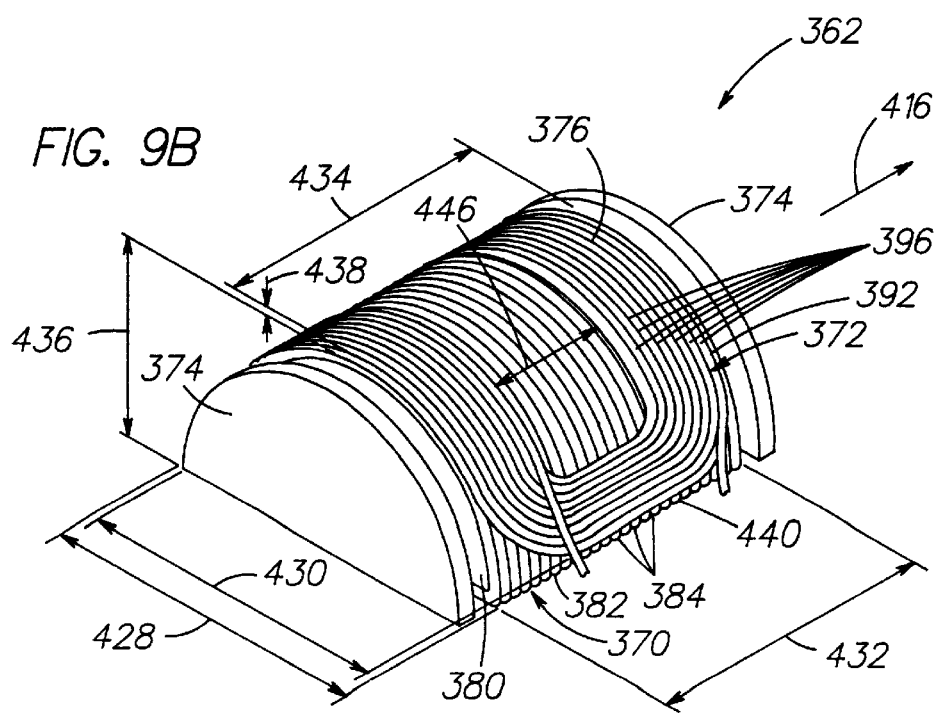
Figure 10A:
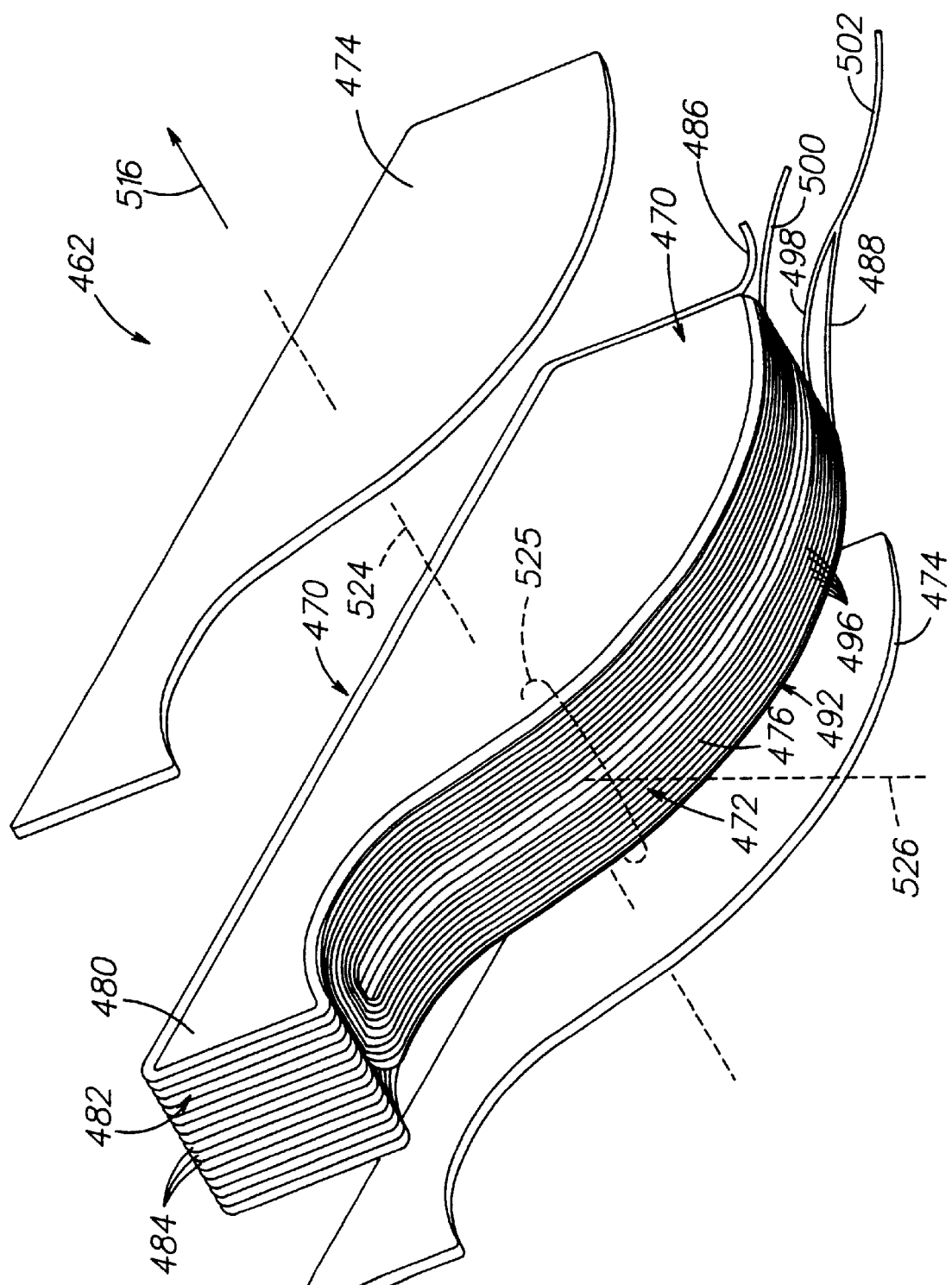
Figure 10B:
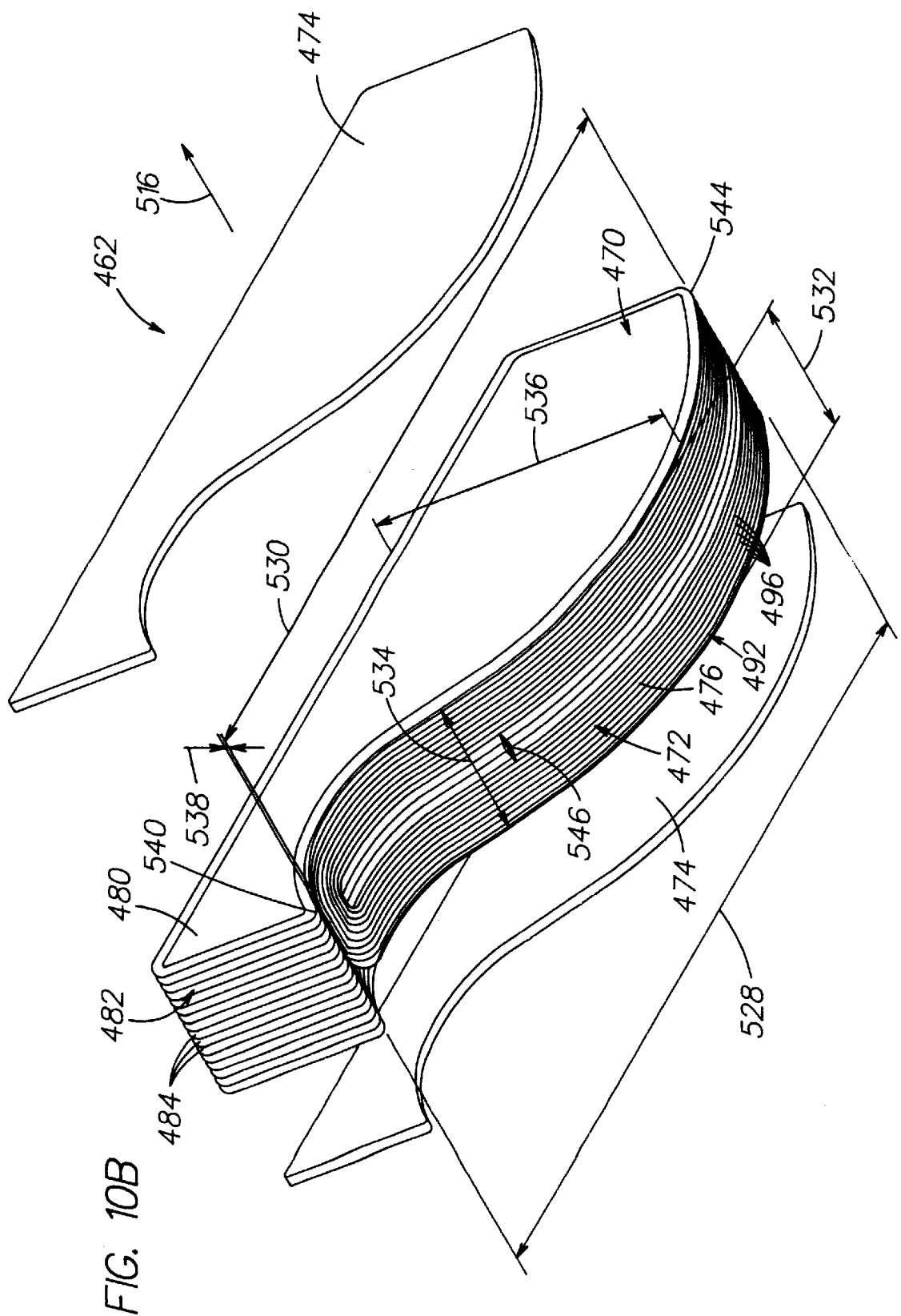

F. 3 is a graph illustrating the magnitude of a response from a conventional eddy current probe to an artificial defect;

FIG. 4 is a graph illustrating the simulated magnitude of a response from a wide field eddy current probe to an artificial defect;

FIG. 5 is a graph illustrating the magnitude of a signal from the probe of FIG. 1A in response to an artificial defect;

FIG. 6 is a graph illustrating the magnitude of a response from a conventional eddy current probe to an artificial defect;

FIG. 7 is a graph illustrating the magnitude of a signal from the probe of FIG. 1A in response to an artificial defect;

FIG. 8A is a perspective view of an eddy current probe element probe according to a second embodiment of the present invention;

FIG. 8B is another perspective view of the eddy current probe element of FIG. 8A;

FIG. 8C is an exploded end view of the eddy current probe element of FIG. 8A;

FIG. 8D is an exploded plan view of the eddy current probe element of FIG. 8A;

FIG. 8E is an exploded side view of the driver core and the receiver of the eddy current probe element of FIG. 8A;

FIG. 9A is a perspective view of an eddy current probe element probe according to a third embodiment of the present invention;

FIG. 9B is another perspective view of the eddy current probe element of FIG. 9A;

FIG. 9C is a top view of the receiver of the eddy current probe element of FIG. 9A;

FIG. 9D is a side view of the eddy current probe element of FIG. 9A;

FIG. 9E is an exploded side view of the driver core and the receiver of the eddy current probe element of FIG. 9A;

FIG. 10A is a perspective view of an eddy current probe element probe according to a fourth embodiment of the present invention; and FIG. 10B is another perspective view of the eddy current probe element of FIG. 10A;

BEST MODE EMBODIMENT FOR CARRYING OUT THE INVENTION

The present invention is disclosed with respect to a best mode embodiment for use in an inspection system for inspecting the surface of an object, e.g., a rotor disk for a gas turbine engine, as illustrated, in FIG. 1A Referring now to FIG. 1A, an automated inspection system 20 for inspecting an object, e.g., a rotor disk 24 for a gas turbine engine (not shown), includes an eddy current probe 28, an interface instrument 32, and a processor 36. The rotor disk 24 may have a hub portion 40 and a disk portion 44 with a common longitudinal axs 48. The hub and the disk portions 40, 44 have surfaces 52, 56 that converge at a corner 58.

The eddy current probe 28 comprises a housing 60, a probe element 62, and an electrical connector 64. The housing 60 has an end 66 with an outer surface 67 and a cavity 68. The probe element 62 comprises a driver 70, a receiver 72, and a pair of shields 74. The receiver has a major outer surface 76. The probe element 62 fits inside the cavity 68 such that major outer surface 76 of the receiver 72 is substantially flush with the outer surface 67 of the end 66 of the housing 60. With the probe element in the cavity, a protective layer, e.g., 0.004 inch thick Teflon tape, is typically provided over the probe element 62 and the outer surface 67 of the housing end to help prevent abrasion, from the surface of the object.

Referring now to FIG. 2A, the driver 70 comprises a core 80 and coil 82. The coil 82 has a plurality of windings 84, disposed around the core 80, and two end terminals 86, 88. The receiver 72 comprises a coil 92 having a plurality of windings 96, two end terminals 98, 100. One end terminal 98 of the receiver coil 92 is preferably electrically connected to one end terminal 88 of the driver coil 82, thereby establishing a common terminal 102.

Referring again to FIG. 1A, the common terminal 102 and the other driver and receiver terminals 86, 100 electrically connect to the interface instrument 32 via the electrical connector and a plurality 104 of electrical conductors. Another plurality of electrical conductors 105 electrically connect the interface instrument 32 to the processor 36.

Figure 1B:
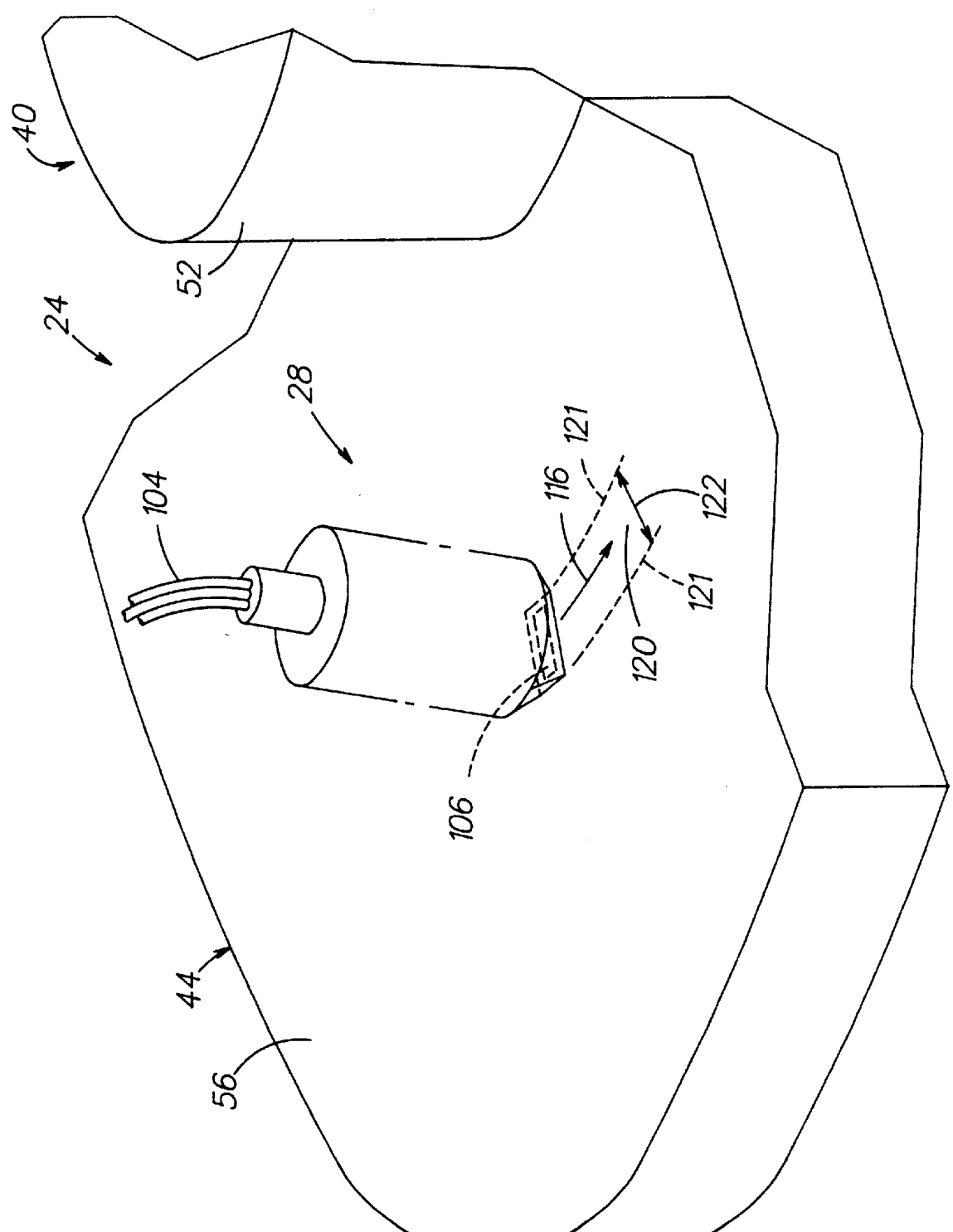
FIG. 1B is an illustration of the eddy current probe and rotor disk of FIG. 1A, with the eddy current probe positioned to inspect the rotor disk.

Referring now to FIG. 1B, an automated manipulator (not shown) positions the eddy current probe 28 adjacent to a surface on the rotor disk 24, e.g., the surface 56 of the disk portion 44, to facilitate inspection of the surface. The manipulator (not shown) orients the eddy current probe 28 such that the major outer surface 76 of the receiver 72 faces toward the surface 56 to be inspected. This orientation facilitates inspection of a surface portion 106, directly opposite, e.g., underneath the major outer surface 76 of the receiver 72, referred to herein as a scan surface 106. The interface instrument 32 provides, to the driver coil 82, an electrical excitation signal that results in a magnetic field from the driver coil 82. The magnetic field brings about an eddy current in the scan surface 106. The characteristics of the eddy current depend on the characteristics of the scan surface 106, e.g., whether the surface 106 has any defects. The eddy current in the scan surface 106 results in an electrical signal, e.g. current signal, within the receiver coil 92. The electrical signal has characteristics commensurate with those of the eddy current.

The manipulator (not shown) moves the eddy current probe in a path 116, referred to herein as a scanning path 116, generally parallel to the surface 56 of the rotor disk. As the probe moves along a scanning path 116, it scans the surface directly opposite, e.g., underneath, it on the rotor disk, resulting in a cumulative scanned surface 120 outlined by a pair of dotted lines 121. The cumulative scanned surface has a width 122.

The interface instrument 32 monitors the electrical signal within the receiver coil 92 and provides, to the processor 36, electrical signals indicative of the characteristics of the electrical signal within the coil 92. The processor 36 processes the signals to determine whether they indicate the presence of defects in the scan surface 106 and cumulative scan surface 120.

Referring again now to FIG. 2A, the eddy current probe element 62 is of the type commonly referred to as an electric current perturbation probe. The driver coil 82 has an effective axis 124. The effective axis 124 is defined herein as a primary apparent axis of the coil 82, being substantially parallel to the primary direction of the magnetic field 125, in the vicinity of the major outer surface 76 of the receiver, resulting from a current through the coil 82. The magnetic field 125 produced by the driver is preferably substantially uniform in the vicinity of the receiver. For a coil having windings of all the same orientation, e.g., similar to that of FIG. 2A, the effective coil axis 124 is substantially coincident with the actual axis of the coil. However, for a coil having windings of various orientations, e.g., a coil described hereinbelow with respect to a third embodiment (FIGS. 9A–9E) the effective coil axis may not coincide with the actual axis. The receiver coil 92 has a coil axis 126 oriented substantially perpendicular to the driver coil axis 124. The perpendicular orientation of the driver and receiver coil axes 124, 126 decouples the receiver from the magnetic field 125 of the driver, thereby making the probe less sensitive to the surface morphology of the object under inspection.

Figure 2B:
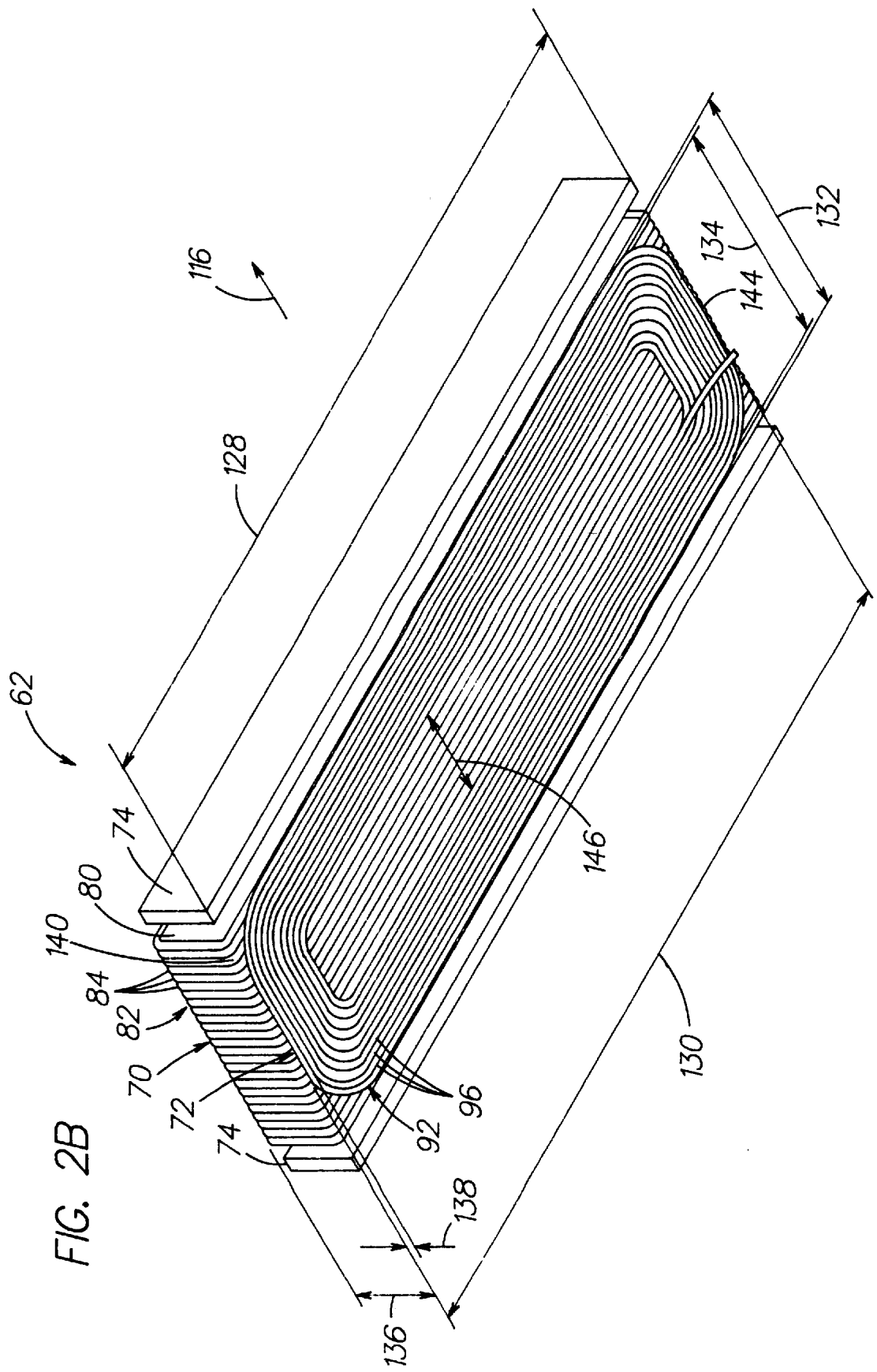
FIG. 2B is another perspective view of the eddy current probe element of FIG. 1A.

Referring now to FIG. 2B, the driver and the receiver coils 82, 92 each have respective widths 128, 130, lengths 132, 134, and thicknesses 136, 138. The driver coil 82 has widthwise opposite edges 140, 144. As is customary for eddy current probes, the width 128, 130 is defined herein as the dimension perpendicular to the direction of the scan path 116. This convention makes the width dimension parallel to the direction of the width 122 (FIG. 1B) of the cumulative scan surface 120 (FIG. 1B). Length 132, 134 is defined herein as the dimension parallel to the direction of the scan path 116. This convention makes the length perpendicular to the direction of the width 122 (FIG. 1B) of the cumulative scan surface 120 (FIG. 1B).

In accordance with a first aspect of the present invention, the receiver 72 has a width 130 dimension that is substantially larger than its length 134 dimension, preferably at least 1.25 times its length so as to provide a wide field of coverage. Increasing the width 130 relative to the length 134, of an eddy current probe, to provide a wide field of coverage typically results in a significant and/or excessive degradation in sensitivity and uniformity. However, it has been determined that for an electric current perturbation type of eddy current probe, it is possible to increase the width 130 relative to the length 134, without resulting in an excessive degradation in sensitivity or uniformity. An increase in length 134 results in a generally proportional decrease in the sensitivity of the receiver, but an increase in width 130 results in a much smaller decrease in sensitivity than that resulting from an increase in the length 134. Thus the receiver 72 may be adapted to provide a wide scan width 122 (FIG. 13) to facilitate a reduction in the inspection time while still providing suitable sensitivity. The width to length ratio should be chosen to best suit the application. The length 134 of the receiver 72 is preferably just large enough to enable a suitable number of windings on the receiver. For example, in one embodiment, the width 130 and length 134 of the receiver 72 are about 0.150 and 0.056 inches respectively, for a ratio of about 2.5:1. In another embodiment, the width 130 and length 134 of the receiver 72 are about 0.500 and 0.056 inches respectively, for a ratio of about 9:1.

In accordance with a second aspect of the present invention, the distance between the receiver 72 and at least one of the widthwise opposite edges 140, 144 is less than 0.125 times the width 128 of the driver 70, thereby providing the probe element 62 with greater sensitivity near the widthwise periphery of the driver than possible with previous electric current perturbation probes. The conventional wisdom regarding perturbation probes has been that the width 128 of the driver 70 must be significantly greater than the width of the receiver in order to generate a sufficiently uniform magnetic field under the receiver 72. As a result traditional perturbation probes have poor sensitivity near their widthwise edges 140, 144. However, it has been determined that the receiver 72 can extend near a widthwise edge 140, 144 of the driver 70 without excessively decreasing the uniformity of the magnetic field under the receiver. With the receiver 72 near the widthwise edge of the driver 70 and a suitable magnetic field under the receiver, there is greater sensitivity near the widthwise edge of the probe. Greater sensitivity near the edge facilitates inspection of components having complex geometries, e.g., discontinuities such as the corner 58 (FIG. 1) on the rotor disk 24 (FIG. 1). The receiver preferably extends from one edge 140 of the driver to the other edge 144 of the driver, to provide maximum sensitivity at both edges 140, 144 of driver 70, however this is not required. Progressive improvement in sensitivity near an edge can be achieved by making the distance between the receiver 72 and the edge progressively smaller, thus a distance of 0.0313 times the width 128 of the driver provides greater sensitivity near the edge than a distance of 0.0625 times the width 128 of the driver.

The receiver coil preferably has a pancake—like shape, defined herein as having width and length dimensions 130, 134 that are much greater than the thickness dimension 138. The receiver coil preferably has only one layer of windings, i.e., the thickness 138 of the receiver coil is substantially equal to the thickness of a winding 96, wherein the windings 96 are arranged in a spiral. The number of windings is preferably in the range of about 5 to about 15, preferably about 10. There is preferably a gap 146, e.g., of about 0.025 inches in width, in the middle of the spiral. Such a receiver results in a probe having optimal sensitivity. The receiver coil 92 preferably comprises 50 gauge copper wire with an enamel insulation, although any suitable electrical conductor may be used. The impedance of the receiver is typically below 10 to 20 ohms at a frequency of 2 mega Hertz (Mhz). Although impedances of greater than 50 ohms are typically desired for a driver and a receiver of an eddy current probe, an impedance 10 to 20 ohms does not present a significant problem for an electric current perturbation type. In some embodiments, the receiver includes a core comprising, for example a ferromagnetic material, that provides the receiver with an impedance of somewhat higher magnitude.

In this embodiment, the driver core 80 has the shape of a rectangular block. The thickness 150 (FIG. 2E) of the core 80 is preferably relatively small, which has the effect of reducing the magnitude of the impedance of the driver so that it may be closer in magnitude to that of the receiver. However, a small thickness does not prevent the driver from providing a suitable magnetic field. In one embodiment, the driver has a thickness of less than 0.1 inches, preferably less than 0.05 inches, more preferably 0.025 inches. The thickness of the core in the best mode embodiment is about 0.0015 inches. When using the probe to inspect an aerospace component, the electrical excitation signal, provided by the interface instrument to the driver coil, typically has a frequency magnitude in a range of about 1 Mhz to about 6 MHz, usually around 5 Mhz. The length of the driver is preferably about the same as that of the receiver although any suitable length may be used.

In the best mode embodiment the driver core 80 comprises a ferrite material, however the core 80 may comprise any suitable material including plastic and air. The driver coil preferably comprises 44 gauge copper wire with an enamel insulation, although any suitable electrical conductor may be used. There is preferably no gap between adjacent windings 84. The number of windings 84 is preferably in a range from about 15 to about 40, although a number range of about 20 to 30, e.g., 25, is more preferred.

The driver 70 and the receiver 72 are fabricated separately and then affixed together. As the driver coil 82 is wound around the core 80, a small amount of adhesive is placed between windings 84 to keep the windings together. The receiver coil 92 is preferably formed atop a sticky, planar, surface, e.g. a planar surface having double sided tape stuck to it (not shown). As the coil 92 is formed, a small amount of adhesive, e.g., an epoxy that cures in about 5 minutes, is placed between the windings 96. The sticky surface keeps the windings in place until the adhesive cures. When the adhesive is adequately cured, the coil 92 is removed from the sticky surface, and affixed to the driver coil 82 by means of a small amount of adhesive placed between the driver and the receiver coils 82, 92. The shields 74 which preferably comprise a ferrite material, may be affixed to the probe element by means of an adhesive, e.g., an epoxy that cures in about 5 minutes.

FIGS. 2C, 2D, 2E, provide additional views of the parts of the eddy current element 62.

Two criteria commonly used for evaluating an eddy current probe include the uniformity of its response, as measured at different points along the width of the probe, referred to herein as uniformity, and the sensitivity of its response, which may be expressed as a signal to noise ratio representing a ratio between the peak to peak signal amplitude and the worst case peak to peak noise. Sensitivity is a qualitative measure that indicates the capability of the probe to detect flaws of a particular size. For a probe to be useful for an application, it must have sufficient sensitivity to detect flaw sizes of interest. Uniformity is an indication of the useful width of the probe. Probes do not have the same sensitivity at all points across the width of the probe. The sensitivity at the edge is typically lower than at the center and may not be suitable for the application. A greater useful width, in effect means that the probe inspects a wider area at one time, referred to as wider field coverage, enabling a more rapid overall inspection. Uniformity is also an indication of the usefulness of the probe for inspecting components having complex geometries, for example those having corners. Typically, the edge is the only part of the probe that can be positioned near a corner. If the probe has low sensitivity at its edges, the probe will not be able to detect a flaw near the corner.

Figure 3:
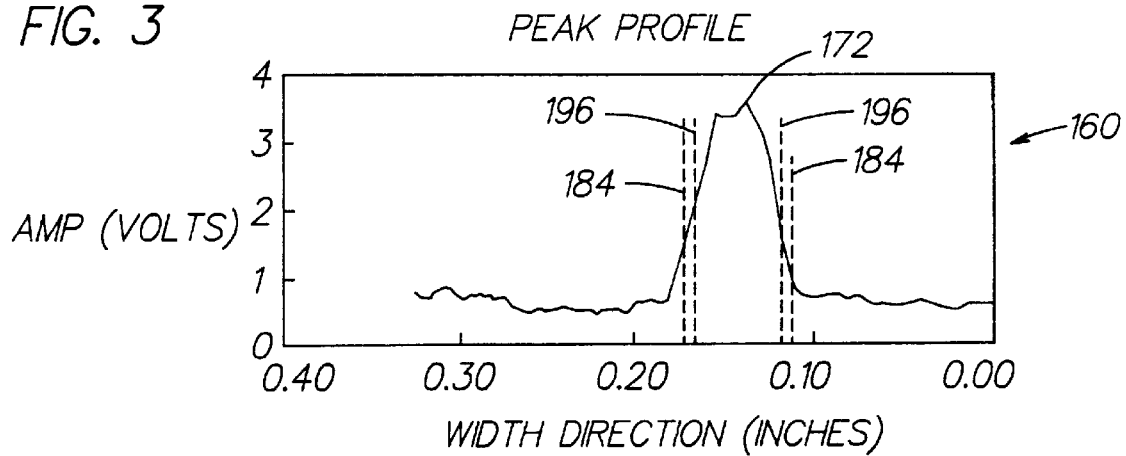

Referring now to FIGS. 3, 4, 5, graphs 160, 164, 168 respectively have curves 172, 176, 180 illustrating the uniformity of the response for each of three different eddy current probes to a small elliptical-shaped defect in a titanium surface. Curve 172 (FIG. 3) represents the response from an eddy current probe (a differential reflection eddy current probe) traditionally used to inspect critical components in the aerospace and power generation industries. Although this probe is small, having a width of only 0.060 inches, it represented the previous largest probe having suitable signal to noise ratio. Curve 176 (FIG. 4) represents the response from a commercially available wide field eddy current probe having a width of about 0.52 inches. Curve 180 (FIG. 5) represents the response from the eddy current probe in a preferred embodiment of the present invention, having a width of about 0.151 inches. Curves 172 (FIG. 3), 180 (FIG. 5) represent actual responses to the defect. Curve 176 (FIG. 4) represents a simulated response to the defect. The elliptical-shaped defect, produced by electrical discharge machining (EDM), measures 0.01 inches deep, 0.02 inches long, i.e., the dimension in the direction of the scan path, and 0.0019 inches wide, i.e., the dimension in the direction perpendicular to the scan path Each of the curves 172 (FIG. 3), 176 (FIG. 4), 180 (FIG. 5) has a pair of dotted lines 184 (FIG. 3), 188 (FIG. 4), 192 (FIG. 5), that identify the magnitude of the response at the widthwise edges of the corresponding probe and another pair of dotted lines 196 (FIG. 3), 200 (FIG. 4), 204 (FIG. 5), that identify the portion of the response where the magnitude is at least 50% of the peak magnitude. Curve 172 (FIG. 3) indicates that the traditional eddy current probe provides a magnitude of at least 50% of the peak magnitude for 0.050 inches of the 0.06 inch wide probe, i.e., 80% of the probe width. Curve 176 (FIG. 4) indicates that the commercially available wide field eddy current probe provides a magnitude of at least 50% of the peak magnitude for 0.30 inches of the 0.52 inch wide probe, i.e., 58% of the probe width. Curve 180 (FIG. 5) indicates that the eddy current probe in a preferred embodiment of the present invention provides a magnitude of at least 50% of the peak magnitude for 0.145 inches of the 0.151 inch wide probe, i.e., 96% of the probe width. Thus, the eddy current probe of the present invention provides a more uniform response than that of the eddy current probe traditionally used in aerospace and power generation industries. In addition, the probe of the present invention provides a more uniform response than the commercially available wide field probe. Furthermore, although the probe in one preferred embodiment is not as wide as the commercially available wide field probe, 0.151 inches compared to 0.52 inches, a probe in another preferred embodiment of the present invention has a width of about 0.50 inches and a response that is nearly as uniform, on a percentage basis, as that of the 0.151 inch wide probe. Thus, such a probe is as wide as the widest commercially available eddy current probe and more uniform in response.

Referring now to FIGS. 6, 7 graphs 208, 212, respectively have curves 216, 220, illustrating the signal to noise ratio of the response, to the defect described above, from the traditional eddy current probe, having a width of 0.06 inches, and the eddy current probe in a preferred embodiment of the present invention, having a width of about 0.151, respectively. The signal to noise ratio of the response from the traditional eddy current probe is 9.3:1. The signal to noise ratio of the response for the eddy current probe of the present invention is 17.0:1. Thus, the eddy current probe of the present invention is not only wider and more uniform in response, it is also has a greater signal to noise ratio than the traditional eddy current probe used to inspect critical components in the aerospace and power generation industries. These attributes result in better flaw sensitivity to enable detection, without generating false calls, of smaller size flaws, and at the same time reduce inspection time by a factor of three. In other embodiments, even greater productivity improvements can be achieved.

The dimensions and the relationships described above in accordance with the first embodiment of the present invention carry forward to the other embodiments described below.

FIGS. 8A–8E, 9A–9E, 10A–10E illustrate different embodiments of the present invention. In each of these embodiments, the core has a shape different than that of the first embodiment, however, the operation of and the interfacing to the probes in each of these embodiments is substantially the same as described above with respect to the first embodiment.

Referring now to FIG. 8A, an eddy current probe 262 according to a second embodiment of the present invention comprises a driver 270, and a receiver 272 with a major outer surface 276. The driver 270 comprises a core 280 and coil 282. The coil 282 has a plurality of windings 284, disposed around the core 280, and two end terminals 286, 288. The receiver 272 comprises a coil 292 having a plurality of windings 296, two end terminals 298, 300. One end terminal 298 of the receiver coil 292 is preferably electrically connected to one end terminal 288 of the driver coil 282, thereby establishing a common terminal 302. The probe is adapted to be moved along a scanning path 316 along the surface of an object.

In this embodiment, the driver core 280 has the shape of a semi-torroid. The thickness 350 (FIG. 8D) of the core 280 is preferably relatively small preferably about 0.0015 inches. In one embodiment, the core has a thickness of less than 0.1 inches, preferably less than 0.05 inches, more preferably about 0.015 inches. The outer diameter of the core is preferably about 0.080 inches.

The driver coil 282 has an effective axis 324, as determined by observing a magnetic field 325 resulting from a current through the coil 282. The receiver coil 292 has a coil axis 326 oriented substantially perpendicular to the driver coil axis 324.

Referring now to FIG. 8B, the driver and the receiver coils each have respective widths 328, 330, lengths 332, 334, and thicknesses 336, 338. The driver coil 282 has widthwise opposite edges 340, 344. As is customary for eddy current probes, the width 328, 330 is defined herein as the dimension perpendicular to the direction of the scan path 316. Length 332, 334 is defined herein as the dimension parallel to the direction of the scan path 316. The length of the driver is preferably a little greater than that of the receiver to provide a more uniform magnetic field under the receiver, although any suitable length may e used. The thickness 336 of the driver is preferably about 0.050 inches. There is preferably a gap 346, e.g., of about 0.025 inches in width, in the middle of the spiral of the receiver coil 292.

In accordance with a first and a second aspect of the present invention, the receiver has a width dimension that is substantially larger than its length dimension, preferably at least 1.25 times its length so as to provide a wider field of coverage; and the distance between the receiver and at least one of the widthwise opposite edges 140, 144 is less than 0.125 times the width of the driver, thereby providing the probe with greater sensitivity near the periphery of the driver than possible with previous electric current perturbation probes.

There is typically no gap between adjacent windings along the radially inner diameter of the driver core 280. However, in some embodiments, it may be desirable to have a gap between the windings along the radially inner diameter of the core, e.g., at the midlength point on the core. The number of windings is preferably in a range from about 30 to 40, e.g., 33.

FIGS. 8C, 8D, 8E, provide additional views of the parts of the eddy current element 262.

Referring now to FIG. 9A, an eddy current probe 362 according to a third embodiment of the present invention comprises a driver 370, a receiver 372, and a pair of shields 374. The receiver has a major outer surface 376. The driver 370 comprises a core 380 and coil 382. The coil 382 has a plurality of windings 384, disposed around the core 380, and two end terminals 386, 388. The receiver 372 comprises a coil 392 having a plurality of windings 396, two end terminals 398, 400. One end terminal 398 of the receiver coil 392 is preferably electrically connected to one end terminal 388 of the driver coil 382, thereby establishing a common terminal 402. The probe is adapted to be moved along a scanning path 416 along the surface of an object.

In this embodiment, the driver core 380 has a substantially semi-cylindrical shape (D-like). This shape results in the major outer surface of the receiver having a curved contour in the width direction, i.e., perpendicular to the scan path, and thereby facilitates scanning of curved surfaces. The radius 450 (FIG. 9E) of the core 380 is preferably relatively small, e.g., about 0.032 inches. Any other suitable shape and size core may also be used.

The driver coil 382 has an effective axds 424, as determined by observing a magnetic field 425 resulting from a current through the coil 382. The receiver coil 392 has a coil axis 426 oriented substantially perpendicular to the driver coil effective axis 424.

Referring now to FIG. 9B, the driver and the receiver coils each have respective widths 428, 430, lengths 432, 434, and thicknesses 436, 438. The driver coil 382 has widthwise opposite edges 440, 444 (not shown). As is customary for eddy current probes, the width 428, 430 is defined herein as the dimension perpendicular to the direction of the scan path 416. Length 432, 434 is defined herein as the dimension parallel to the direction of the scan path 416. The length 432 of the driver is preferably about 0.058 inches. There is preferably a gap 446, e.g., of about 0.025 inches in width, in the middle of the spiral of the receiver coil 392.

In accordance with a first and a second aspect of the present invention, the receiver has a width dimension that is substantially larger than its length dimension, preferably at least 1.25 times its length so as to provide a wider field of coverage; and the distance between the receiver and at least one of the widthwise opposite edges 440, 444 is less than 0.125 times the width of the driver, thereby providing the probe with greater sensitivity near the periphery of the driver than possible with previous electric current perturbation probes.

There is typically no gap between adjacent windings 384 of the driver core 380. The number of windings 384 is preferably in a range from about 15 to about 40, although a number range of about 20 to 30, e.g., 25, is more preferred.

FIGS. 9C, 9D, 9E, provide additional views of the parts of the eddy current element 362.

Referring now to FIG. 10A, an eddy current probe 462 according to a 30 fourth embodiment of the present invention comprises a driver 470, a receiver 472, and a pair of shields 474. The receiver has a major outer surface 476. The driver 470 comprises a core 480 and coil 482. The coil 482 has a plurality of windings 484, disposed around the core 480, and two end terminals 486, 488. The receiver 472 comprises a coil 492 having a plurality of windings 496, two end terminals 498, 500. One end terminal 498 of the receiver coil 492 is preferably electrically connected to one end terminal 488 of the driver coil 482, thereby establishing a common terminal 502. The probe is adapted to be moved along a scanning path 516 along the surface of an object.

In this embodiment, the driver core 480 has a shape with a compound curvature. This shape results in the major outer surface of the receiver having a compound curved contour in the width direction, i.e., perpendicular to the scan path, and thereby facilitates scanning of compound curved surface. The radius 450 (FIG. 9E) of the core 380 is preferably relatively small, e.g., about 0.032 inches. Any other suitable shape and size core may also be used.

The driver coil 482 has an effective axds 524, as determined by observing a magnetic field 525 resulting from a current through the coil 482. The receiver coil 492 has a coil axis 526 oriented substantially perpendicular to the driver coil effective axis 524.

Referring now to FIG. 10B, the driver and the receiver coils each have respective widths 528, 530, lengths 532, 534, and thicknesses 536, 538. The driver coil 482 has widthwise opposite edges 540, 544. As is customary for eddy current probes, the width 528, 530 is defined herein as the dimension perpendicular to the direction of the scan path 516. Length 532, 534 is defined herein as the dimension parallel to the direction of the scan path 516. There is preferably a gap 546, e.g., of about 0.025 inches in width, in the middle of the spiral of the receiver coil 492.

In accordance with a first and a second aspect of the present invention, the receiver has a width dimension that is substantially larger than its length dimension, preferably at least 1.25 times its length so as to provide a wider field of coverage; and the distance between the receiver and at least one of the widthwise opposite edges 540, 544 is less than 0.125 times the width of the driver, thereby providing the probe with greater sensitivity near the periphery of the driver than possible with previous electric current perturbation probes.

There is typically no gap between adjacent windings 484 of the driver core 480. The number of windings 484 is preferably in a range from about 15 to about 40, although a number range of about 20 to 30, e.g., 25, is more preferred.

It should be understood that although the best mode embodiment incorporates the first and the second aspects of the present invention, this is not required. Thus, a probe may incorporate only the first aspect or only the second aspect or a combination of the first and second aspects. Optimum sensitivity is typically achieved by orienting the scan path in a direction parallel to the direction of the greater surface dimension of the expected defect.

Furthermore, it should also be understood that although the present invention is disclosed with respect to embodiments disclosing drivers and receivers having particular shapes and dimensions, the present invention may be used with drivers and receivers of any shapes and dimensions. For example, other embodiments may employ a driver having a serni-torroidal-like shape (similar to the shape of the driver 270 in FIGS. 8A–E), and a receiver having a semi-cylindrical-like shape core (similar to the shape of the driver core 380 in FIGS. 9A–9E) or a rectangular shape core (similar to the shape of the driver core 80 in FIGS. 2A–2E), wherein the receiver coils are wound around the core so as so make the coil axis substantially perpendicular to the effective axis of the driver coil.

While the particular invention has been described with reference to various embodiments, this description is not meant to be construed in a limiting sense. It is understood that various modifications of the above embodiments, as well as additional embodiments of the invention, will be apparent to persons skilled in the art upon reference to this description, without departing from the spirit of the invention, as recited in the claims appended hereto. It is therefore contemplated that the appended claims will cover any such modifications or embodiments as fall within the true scope of the invention.

What is claimed is:

1. An eddy current probe for use in inspecting an object, where the probe is moved along a scan path relative to the object, the probe comprising:
   a driver having a coil with an effective coil axis, said driver having a length and a width, said length being the dimension in a direction substantially parallel to the scanning path; and
   a receiver having a coil with a coil axis oriented substantially perpendicular to said driver coil effective coil axis, said receiver having a length, a width, and a thickness, said length being the dimension in the direction parallel to the scanning path, said width having a dimension substantially greater than that of said length.

2. The probe of claim 1 wherein said width of said probe is at least 1.25 times its length.

3. The probe of claim 1 wherein said width of said probe is at least 2.5 times its length.

4. The probe of claim 1 wherein said receiver is disposed between the object and said driver.

5. The probe of claim 1 wherein said receiver has a pancake-like shape.

6. The probe of claim 1 wherein said receiver coil has a number of windings in a range of from about 5 to about 15.

7. The probe of claim 1 wherein said receiver coil has a gap of about 0.025 inches.

8. The probe of claim 1 wherein said driver has a height less than 0.1 inches.

9. The probe of claim 1 wherein said coil of said driver has widthwise opposite edges and the magnitude of the distance between the receiver and at least one of said edges is less than 0.125 times the width of said driver.

10. The probe of claim 1 wherein said coil of said driver has widthwise opposite edges and the magnitude of the distance between the receiver and at least one of said edges is less than 0.0625 times the width of said driver.

11. The probe of claim 1 wherein said width of said probe is at least 1.25 times its length, said receiver having a pancake-like shape, said receiver coil having a number of windings in a range of from about 5 to about 15, said driver having a height less than 0.1 inches, and said receiver being disposed between the object and said driver.

12. The probe of claim 11 wherein said coil of said driver has widthwise opposite edges and the magnitude of the distance between the receiver and at least one of said edges is less than 0.125 times the width of said driver.

13. The probe of claim 11 wherein said coil of said driver has widthwise opposite edges and the magnitude of the distance between the receiver and at least one of said edges is less than 0.0625 times the width of said driver.

14. The probe of claim 1 wherein said receiver has a major outer surface with a substantially curved contour i n the width direction.

15. The probe of claim 1 wherein said receiver has a major outer surface with a substantially compound curved contour in the width direction.

16. An eddy current probe for use in inspecting an object, where the probe is moved along a scan path relative to the object, the probe comprising:
   a driver having a coil with an effective coil axis, said driver having a length and a width, said length being the dimension in a direction substantially parallel to the scanning path, said coil of said driver having widthwise opposite edges; and
   a receiver having a coil with a coil axis oriented substantially perpendicular to said driver coil effective coil axis, said receiver having a length, a width, and a thickness, said length being the dimension in the direction parallel to the scanning path, where the magnitude of a distance between said receiver and at least one of said edges is substantially less than about 0.125 times the width of said driver.

17. The probe of claim 16 wherein the magnitude of the distance between the receiver and at least one of said edges is less than about 0.0625 times the width of said driver.

18. The probe of claim 16 wherein said receiver is disposed between the object and said driver.

19. The probe of claim 16 wherein said receiver has a pancake-like shape.

20. The probe of claim 16 wherein said receiver coil has a number of windings in a range of from about 5 to about 15.

21. The probe of claim 16 wherein said receiver coil has a gap of about 0.025 inches.

22. The probe of claim 16 wherein said driver has a height less than 0.1 inches.

23. The probe of claim 16 wherein said receiver has a pancake-like shape, said receiver coil having a number of windings in a range of from about 5 to about 15, said driver having a height less than 0.1 inches, and said receiver being disposed between the object and said driver.

24. Th e probe of claim 16 wherein said receiver has a major outer surface with a substantially curved contour in the width direction.

25. The probe of claim 16 wherein said receiver has a major outer surface with a substantially compound curve d contour in the width direction.

26. A method for inspecting an object along a scan path relative to the object, the method comprising:

providing an eddy current probe having
- a driver having a coil with an effective coil axis, said driver having a length and a width, said length being the dimension in a direction substantially parallel to the scanning path, and
- a receiver having a coil with a coil axis oriented substantially perpendicular to said driver coil effective coil axis, said receiver having a length, a width, and a thickness, said length being the dimension in the direction parallel to the scanning path, said width having a dimension substantially greater than that of said length;

moving said eddy current probe substantially along the scan path, wherein said eddy current probe produces an electrical signal indicative of the presence of flaws in the object; and presenting said electrical signal from said eddy current probe.

27. The method of claim 26 further comprising the step of monitoring said electrical signal from said eddy current probe and generating electrical signals indicative of said signal from said eddy current probe; and processing said generated electrical signals to determine the presence of defects in the object.

28. A method for inspecting an object along a scan path relative to the object, the method comprising:

providing an eddy current probe having
- a driver having a coil with an effective coil axis, said driver having a length and a width, said length being the dimension in a direction substantially parallel to the scanning path, said coil of said driver having widthwise opposite edges,
- a receiver having a coil with a coil axis oriented substantially perpendicular to said driver coil effective coil axis, said receiver having a length, a width, and a thickness, said length being the dimension in the direction parallel to the scanning path, where the magnitude of a distance between said receiver and at least one of said edges is less than 0.125 times the width of said driver;

moving said eddy current probe substantially along the scan path, wherein said eddy current probe produces an electrical signal indicative of the presence of flaws in the object; and presenting said electrical signal from said eddy current probe.

29. The method of claim 28 further comprising the step of monitoring said electrical signal from said eddy current probe and generating electrical signals indicative of said signal from said eddy current probe; and processing said generated electrical signals to determine the presence of defects in the object.

* * * * *